(12) United States Patent
Magnusson et al.

(10) Patent No.: US 6,235,966 B1
(45) Date of Patent: May 22, 2001

(54) ABSORBENT STRUCTURE, AND PRODUCTION OF ABSORBENT STRUCTURE BY MAT FORMATION ON HIGH-LOFT MATERIAL

(75) Inventors: Ing-Britt Magnusson, Mölnlycke; Johanna Pålsson, V. Frölunda, both of (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/194,438
(22) PCT Filed: May 23, 1997
(86) PCT No.: PCT/SE97/00851
  § 371 Date: Nov. 25, 1998
  § 102(e) Date: Nov. 25, 1998
(87) PCT Pub. No.: WO97/45084
  PCT Pub. Date: Dec. 4, 1997

(30) Foreign Application Priority Data

May 31, 1996 (SE) .................................................... 9602155

(51) Int. Cl.[7] .............................. A61F 13/15; A61F 13/20
(52) U.S. Cl. ........................ 604/374; 604/365; 604/367; 604/375
(58) Field of Search .................................. 604/374, 384, 604/365, 367, 366, 375, 379, 370, 378; 128/287; 156/62.2, 62.4, 62.8; 264/109; 428/323, 326

(56) References Cited

U.S. PATENT DOCUMENTS

| | | |
|---|---|---|
| 4,129,132 | 12/1978 | Butterworth et al. ............... 128/287 |
| 4,655,757 | 4/1987 | McFarland et al. ................. 604/366 |
| 5,356,405 | * 10/1994 | Thompson et al. .................. 604/384 |
| 6,100,441 | * 8/2000 | Blomstrom et al. ................. 604/367 |
| 6,127,594 | * 10/2000 | Rosseland ............................. 604/365 |

FOREIGN PATENT DOCUMENTS 479442  4/1992  (EP) .

* cited by examiner

*Primary Examiner*—Glenn K. Dawson
*Assistant Examiner*—Michele Kidwell
(74) *Attorney, Agent, or Firm*—Young & Thompson

(57) ABSTRACT

Absorbent structure (1) consisting of an absorbent material layer (2) of cellulose fibers (4) and a high-loft material layer (3) of synthetic fibers (5), and a method for producing an absorbent structure (1) which is intended for use in an absorbent article. The two layers are held together by being integrated in each other by the fibers (4) of the absorption material (2) extending into cavities in the high-loft material (3). In this method, the absorbent material (2) is mat-formed directly on a high-loft material (3), which is placed on a wire (26). Arranged under the wire (26) there is a suction box (22) which sucks air downwards, the fibers (4) being sucked downwards and penetrating down into the high-loft material (3).

13 Claims, 2 Drawing Sheets

ABSORBENT STRUCTURE, AND PRODUCTION OF ABSORBENT STRUCTURE BY MAT FORMATION ON HIGH-LOFT MATERIAL

This is the 35 USC 371 national stage of international application PCT/SE97/00851 filed on May 23, 1997, which designated the United States of America.

BACKGROUND

The present invention relates to an absorbent structure consisting of an absorbent material layer and a high-loft material layer, and to a method for producing an absorbent structure which is intended for use in an absorbent article, such as a sanitary towel, panty liner, incontinence pad, diaper, bandage, saliva absorber, or the like.

Absorbent articles of this type are known in a large number of designs. The absorption body in these products can be produced by means of cellulose pulp, for example in rolls, bales or sheets, being dry-defibered and converted in fluffed form to a pulp to a pulp mat, sometimes with admixture of so-called superabsorbents, which are polymers having the ability to absorb several times their own weight of water or bodily fluid.

The pulp body is often compressed, on the one hand in order to increase its ability to spread liquid, and on the other hand to reduce the bulk of the pulp body and obtain a product which is as compact as possible.

It is of great importance for these products that they have a high absorption capacity, that the total absorption capacity is fully utilized, and that the materials included have a good ability to spread the absorbed liquid. The product should also be thin so that it can be used as discreetly as possible.

SE,B,462 622 describes a readily disintegratable product comprising cellulose-containing fibre material, which product is of such a strength that it can be rolled up or handled in sheet form for storage and transportation, without addition of chemicals which increase the bonding strength between the fibres. Flash-dried fibres of a chemithermomechanical pulp, so-called CTMP, with a dry matter content of about 80%, are formed into a web. The fibres are conveyed by an air stream, in a controlled flow, through a forming head arranged over a wire. The air is sucked off through a suction box arranged under the wire. The web is pre-pressed in order to reduce the web bulk prior to the final pressing to a density of 550–1000 kg/m³. This product is easy to dry-defibre and to convert to fluffed form for production of, for example, hygiene articles such as diapers, sanitary towels and similar products. The advantage of the material is that the cellulose pulp in roll form is flash-dried and dry-formed into a web, and the pulp thus has a low content of paper bondings, for which reason the defibering energy is lower than for conventional wet-formed pulp. This also affords possibilities of compressing the material hard, inter alia for reducing the transportation and storage volumes, etc., while retaining the low defibering energy. Another advantage is that superabsorbents can be mixed into the dry-formed material, something which is not possible as regards wet-formed material.

It has been found that this dry-formed material in the non-defibered state is a very good absorption material, and it is possible for the material to be used directly, without defibering, as an absorption material in hygiene articles. This is disclosed in the applications SE 9203445-3 and SE 9203446-1. The material also has good spreading properties and swelling properties. A simpler and less costly production process is achieved, and the conventional defibering and the conventional mat formation are not required. For certain product applications in hygiene articles, it is expedient for dry-formed roll pulp to undergo softening prior to use as absorption material. The good absorption properties and swelling properties already mentioned are not affected to any great extent by the softened process.

An absorbent structure often has an admission layer/transport layer on top of an absorbent material layer. The admission layer/transport layer can be a high-loft material (see EDANA definition) which is produced by, for example, through-air bonding (see definition of through-air thermal bonding in EDANA) and consists of synthetic fibres such as polyester, polypropylene or mixtures thereof. A mat of fibres is carded out to form an open layer and is allowed to pass through an oven. The fibres have different melt points and the heat therefore affects the different fibres in account of the fact that some of the fibres melt. Those fibres which do not melt retain an open and aired structure.

When an admission layer/transport layer in the form of a high-loft material or the like is to be bound to an absorption material layer, this must be done in such a way that, on the one hand, the high-loft material fixes in the absorption material layer, and, on the other hand, the transfer of liquid from the high-loft material to the absorption material is not impeded. The normal procedure is quite simply to lay a high-loft material layer directly on the absorbent material layer.

One problem is that the contact between the two layers may become poor. The transfer of liquid from the high-loft material to the absorption material then deteriorates, which is a serious disadvantage for this type of product. It is also conceivable to glue the high-loft material on, but glue impairs the transfer of liquid.

Another problem is that the poor contact between the layers results in the product being of poor strength. The layers can detach from each other and the absorption material can be delaminated.

The object of the invention is to solve these problems.

BRIEF DISCLOSURE OF THE INVENTION

The invention relates on the one hand to an article which is an absorbent structure consisting of an absorbent material layer and a high-loft material, and on the other hand to a method for producing an absorbent structure.

During production, the mat formation of the absorbent material takes place directly on a layer of high-loft material. The fibres from the absorbent material penetrate down into the high-loft material and a strong connection between the high-loft material and the absorbent material is obtained. The layers integrate with each other, which increases the strength of the absorbent structure. The fibres of the absorption material, which extend into the high-loft material, also facilitate the transfer of liquid from the high-loft material to the absorbent material layer, where the fibres will drain the high-loft material.

The article is an absorbent structure in which the high-loft material layer and the absorbent material layer are integrated in each other. The absorption material consists of cellulose fibres and the high-loft material consists of synthetic fibres. The two layers are integrated in each other by means of the fibres from the absorbent material layer extending into cavities in the high-loft material layer. This leads to greater strength and improved transfer of liquid from the high-loft material to the absorbent layer.

DESCRIPTION OF THE INVENTION

The absorbent structure according to the invention consists of an admission layer/transport layer and of an absorption material layer beneath the latter. The admission layer consists of a high-loft material which can be produced by, for example, through-air bonding or needling. This layer consists of synthetic fibres which do not absorb liquid, that is to say the layer is hydrophobic. The admission layer has an open and aired structure and has to quickly admit a given amount of liquid which is simply held loosely in the fibre structure of the high-loft material and has to be quickly drained off, the liquid being conveyed to the absorbent material layer.

Figure 4:
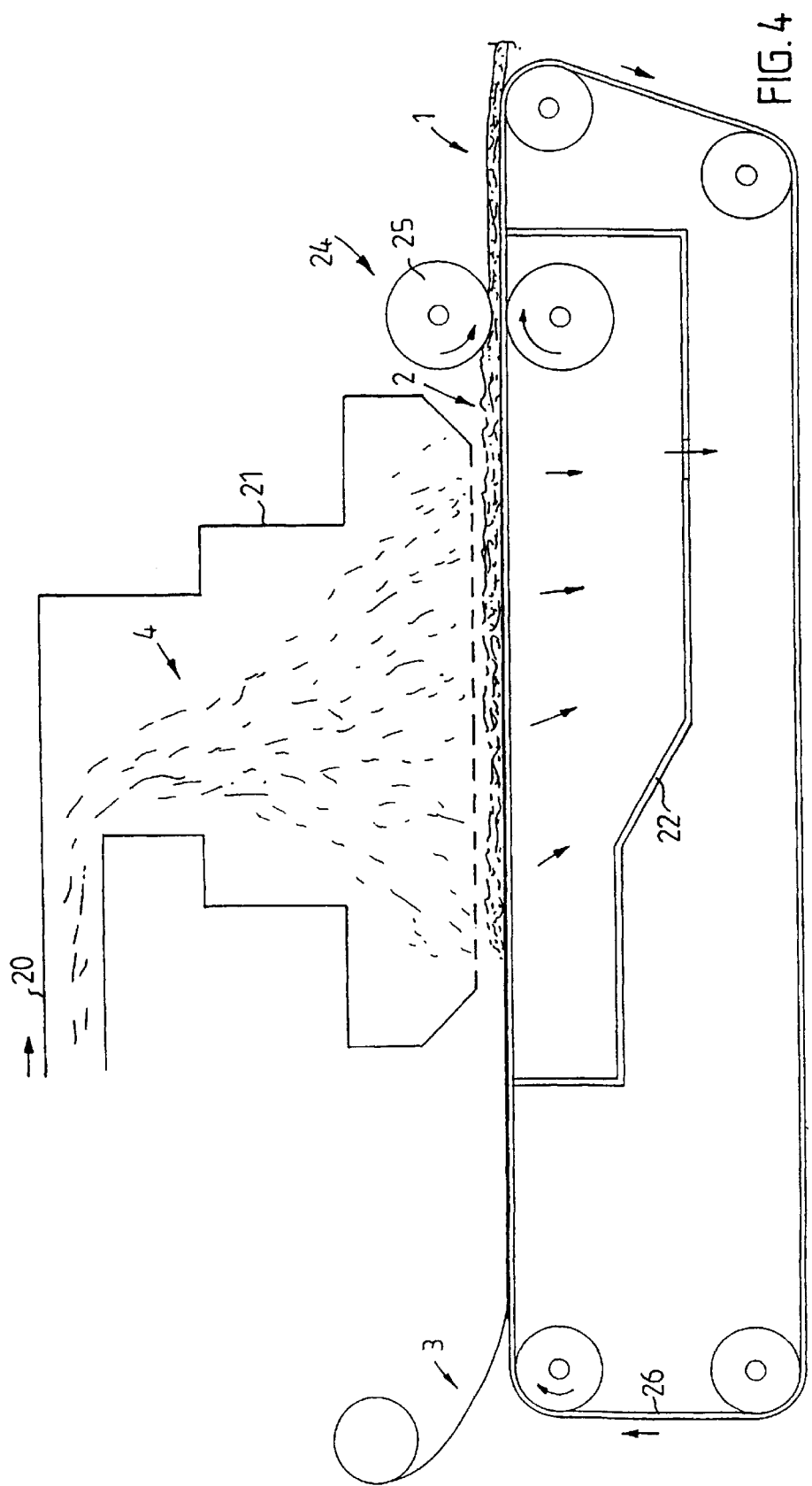
FIG. 4 shows the production of an absorbent structure.

The production of the absorbent structure (1) according to the invention is shown FIG. 4. An absorbent material (2) is mat-formed directly on a layer of high-loft material (3). The high-loft material (3) is laid on a wire (26) and the absorbent material (2) is formed, for example, by means of flash-dried fibres (4) of CTMP being formed into a mat (2). The fibres (4) are in this case conveyed by an air stream (20), in a controlled flow, through a forming head (21) arranged over a wire (26). Arranged under the wire (26) there is a suction box (22) which sucks the air off, the CTMP fibres (4) being sucked downwards and penetrating into the high-loft material (3). The high-loft material (3) and the absorption material (2) are in this way integrated in each other. A strong connection is obtained between the two layers, as well as better admission of liquid from the high-loft material to the absorption material. The fibres (4) of the absorbent material (2) which extend into the high-loft material (3) will function as means of draining the high-loft material. The web is compressed (24) between rollers (25) and the absorbent material acquires a density of 0.2–1 $g/cm^3$ and a grammage of 30–2000 $g/m^2$, which gives a thin product with very good absorption properties. A suitable density for the absorbent material is 0.1–1 $g/cm^3$, in particular 0.2–0.95 $g/cm^3$, preferably 0.25–0.9 $g/cm^3$, and most preferably 0.3–0.85 $g/cm^3$, and a suitable grammage is 30–2000 $g/m^2$, preferably 50–1500 $g/m^2$, and most preferably 100–1000 $g/m^2$. On account of the elasticity of the synthetic fibres, the high-loft material retains the open and aired structure despite the high pressure which arises during the compression following the mat formation. It is also possible to add superabsorbents in the stage of mat formation of the absorbent material layer.

The absorption material can also be formed of fibres from thermomechanical pulp TMP, high-temperature chemithermomechanical pulp HTCTMP, sulphite pulp or kraft pulp.

A surface layer, for example nonwoven, is now generally laid on the high-loft material as an upper layer, when it is to be used in an absorbent article. This can be done either before or after the high-loft material is brought together with the absorbent material layer. In an alternative embodiment of the invention, the high-loft material, together with the surface layer, which is usually fixed to the high-loft material by glue, is then laid on a wire, after which the mat formation is carried out in accordance with the method described above.

Figure 1:
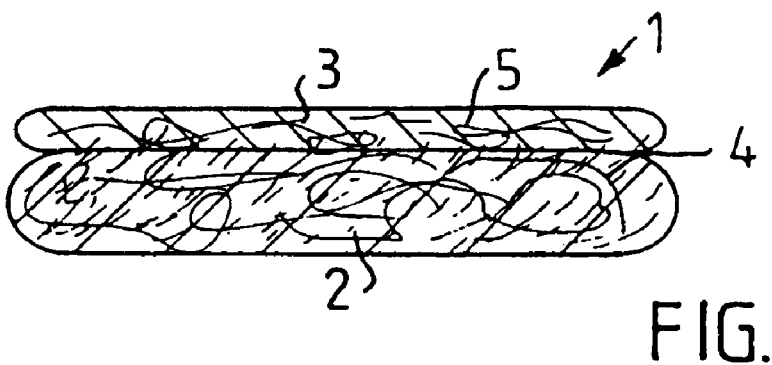
FIG. 1 shows an absorbent structures with an absorbent layer and a high-loft material on top of it, where the fibres of the absorbent layer extend into the high-loft material. The figure is not to scale.

The absorbent structure (1) according to the invention, which is shown if FIG. 1, consists of an absorbent material (2) of cellulose fibres (4), a high-loft material (3) of synthetic fibres (5), where the two materials are integrated in each other. The high-loft material (3) here is placed on top of the absorption material (2). During production, the high-loft material will be at the bottom as the absorption material is formed on top of the high-loft material. The two layers are integrated in each other by means of the fibres (4) of the absorption material (2) extending into cavities in the high-loft material (3). The absorbent material has a density of 0.1–1 $g/cm^3$, in particular 0.2–0.95 $g/cm^3$, preferably 0.25–0.9 $g/cm^3$, and most preferably 0.3–0.85 $g/cm^3$, and a grammage of 30–2000 $g/m^2$, preferably 50–1500 $g/m^2$, and most preferably 100–1000 $g/m^2$.

When the fibres from the absorbent layer extend into the high-loft material, they suck the liquid out of the latter and into themselves. The liquid is held loosely in the fibre structure of the high-loft material and is conveyed through the fibres over to the absorbent material layer where it is absorbed and spread.

The bonding between the two layers is stronger than before, and they are held together by means of the integration between the two layers.

The cellulose fibres in the absorption material consist, for example, of flash-dried fibres of chemithermomechanical pulp CTMP. Other examples of fibres which can be used in the absorption material are fibres from thermomechanical pulp TMP, high-temperature chemithermomechanical pulp HTCTMP, sulphite pulp or kraft pulp.

An absorbent article generally consists also of a surface layer at the top and a liquid-impermeable layer at the bottom. The surface layer, for example nonwoven, which lies on a roll in a machine is coated with glue, the absorbent structure is added, and the bottom layer, for example polyethylene film, is finally laid thereon. In this operation there is a risk of deformation of the absorbent structure, which can lead to the high-loft material losing contact with the absorbent material.

During use of an article in the form of, for example, a diaper or a sanitary towel, there is again a risk of the article being deformed, which can also lead to the high-loft material losing contact with the absorbent material layer.

An advantage of the invention is the stronger connection which is obtained between the two layers as they are integrated with each other. A product with a greater degree of strength is thus obtained.

The admission layer/transport layer has the function of quickly admitting a given amount of liquid, which is only held loosely in the fibre structure of the high-loft material, and must be drained off quickly, whereupon the liquid is conveyed to the absorbent material layer. A disadvantage of the high-loft material is that it does not possess its own suction force. By virtue of the fact that the fibres of the absorbent material layer extend into the high-loft material, the high-loft material draws the liquid more easily to itself.

Even though the absorbent material has very good absorption properties, it does have a disadvantage. It does not admit liquid so well if it has become greatly compressed. The material becomes very tight, and when the surface of the absorbent material layer is so tight, it has a low absorbency. This is remedied by the invention by means of the transfer of liquid from the high-loft material to the absorbent layer being improved. As the fibres project individually or in groups into the high-loft material, they suck the liquid from the high-loft material to themselves and into the compact absorbent material.

An advantage of the dry-formed absorption material is that it is possible to admix superabsorbents therein. As superabsorbents are to be included in the absorbent structure, they are mixed with the absorbent material. The high-loft material then functions as a barrier layer for the superabsorbents, both during production and upon use of an absorbent structure in an absorbent article. During production, the high-loft material layer lies on the wire under the fibres and the superabsorbents, where they prevent the superabsorbents from being sucked out of the absorbent material layer. Upon use of the absorbent structure, the high-loft material layer can function as a barrier layer if it is placed over the absorbent material layer. The superabsorbents are then prevented from moving out in the direction towards the user when the superabsorbents have sucked liquid to themselves.

For certain product applications in hygiene articles, it is expedient to have the absorbent material undergo softening prior to use as absorption material. The previously mentioned good absorption properties, spreading properties and swelling properties are not affected to any great extent by the softening process. Different softening methods include working between rollers, softening by ultrasound, moistening, or chemical additives.

The invention need not be limited to the absorbent material being produced from flash-dried fibres of CTMP which are formed into a layer. Other examples are fibres of TMP, HTCTMP, kraft pulp or sulphite pulp.

The absorbent material layer can then also be formed by conventional mat formation. In conventional mat formation, pulp in the form of sheets, rolls or bales is dry-defibered or torn. The released fibres in the form of fluff are then blown down in discrete forms or on a web. In the production of diapers, use is made of discrete forms with perforated bases. According to the invention, the high-loft material is laid on the base and the fibres are conveyed down into the form. Compression and mat formation of the fibres are carried out in a conventional manner.

Illustrative embodiment

Figure 2:
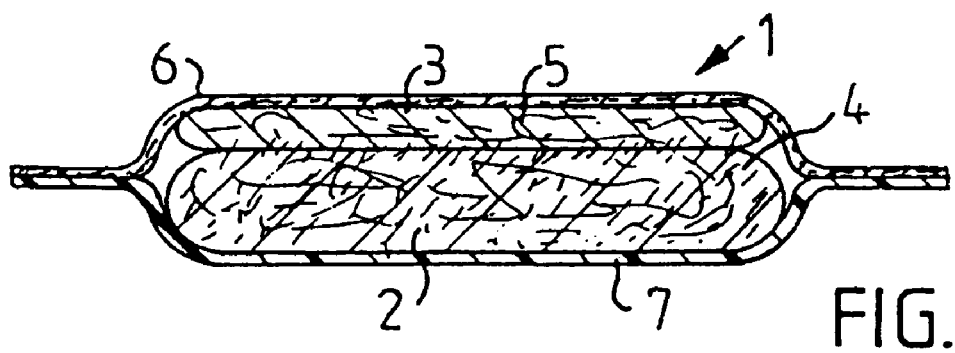
FIGS. 2 and 3 show a diagrammatic layout of an illustrative embodiment with an absorbent structure according to the invention, placed in an article. The figures are not to scale.

FIG. 2 shows an embodiment of an absorbent structure (1) in a diaper. The absorbent structure (1) consists of a high-loft material (3) and an absorbent material (2) which are integrated in each other. They are integrated by means of the fibres (4) of the absorption material (2) penetrating into cavities in the high-loft material (3). At the top of the article there is a liquid-permeable upper layer (6), for example nonwoven, which is directed towards the user during use. At the bottom there is a liquid-impermeable bottom layer (7), for example of polyethylene. The layers (6) and (7) have parts which extend beyond the absorbent structure (1) and they are joined to each other in these parts.

The purpose of the high-loft material is to quickly admit an amount of liquid, and this liquid must only be held loosely in the fibre structure of the high-loft material. By way of the fibres which penetrate into the high-loft material from the absorbent material layer, the liquid is sucked into the absorbent material layer, where the liquid is spread out and stored.

Figure 3:
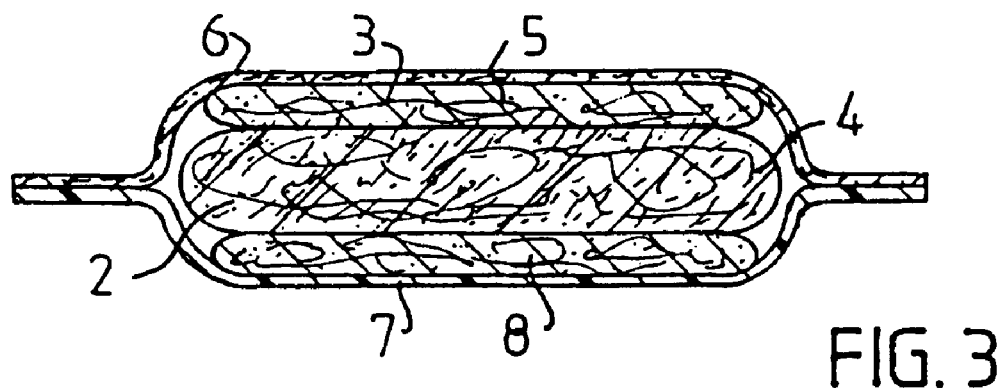

Another illustrative embodiment is shown in FIG. 3, where there is a further absorbent material layer (8). Otherwise, it is like the product in FIG. 2.

The invention is not limited to the illustrative embodiments shown, and instead is applicable to other embodiments.

What is claimed is:

1. A method for producing an absorbent structure consisting of an absorbent material layer and a high-loft material layer, for use in an absorbent article selected from the group consisting of a diaper, a sanitary towel, a panty liner, an incontinence pad, and a bed protector, the method comprising: mat-forming the absorbent material layer consisting of dry fibres of cellulose pulp, directly on the high-loft material layer, so that the dry fibres of the absorbent material layer will penetrate down into cavities of the high-loft material layer, said absorbent material layer having a density of 0.1–1 $g/cm^3$, and a grammage of 30–2000 $g/m^2$.

2. The method according to claim 1, wherein the absorbent material layer is mat-formed by flash-dried fibres of CTMP formed into a mat, the fibres being conveyed by an air stream, in a controlled flow, through a forming head arranged over a wire on which the high-loft material layer is placed.

3. The method according to claim 2, wherein arranged under the wire, there is a suction box which sucks the air off, the CTMP fibres being sucked downwards and penetrating into the high-loft material layer.

4. The method according to claim 3, wherein the absorbent material layer has a density of 0.2–0.95 $g/cm^3$, and a grammage of 50–1500 $g/m^2$.

5. The method according to claim 4, wherein the absorbent material layer has a density of 0.25–0.9 $g/cm^3$, and a grammage of 100–1000 $g/m^2$.

6. The method according to claim 5, wherein the absorbent material layer has a density of 0.3–0.85 $g/cm^3$.

7. An absorbent structure, for use in an absorbent article selected from the group consisting of a diaper, a sanitary towel, a panty liner, an incontinence pad, and a bed protector, the absorbent structure consisting of an absorbent material layer of cellulose fibres and a layer of high-loft material, the absorbent material layer having a density of 0.1–1 $g/cm^3$ and a grammage of 30–2000 $g/m^2$, and wherein the layer of high-loft material and the absorbent material layer are integrated in each other by the fibres of the absorbent material layer extending into cavities in the high-loft material layer.

8. The absorbent structure according to claim 7, wherein the absorbent material layer consists of flash-dried fibres of CTMP.

9. The absorbent structure according to claim 7, wherein the absorbent material layer consists of fibres of TMP, HTCTMP, kraft pulp or sulphite pulp.

10. The absorbent structure according to claim 7, wherein the absorbent material layer consists of fibres of TMP, HTCTMP, kraft pulp or sulphite pulp.

11. The absorbent structure according to claim 7, wherein the absorbent material layer has a density of 0.2–0.95 $g/cm^3$, and a grammage of 50–1500 $g/m^2$.

12. The absorbent structure according to claim 11, wherein the absorbent material layer has a density of 0.25–0.9 $g/cm^3$, and a grammage of 100–1000 $g/m^2$.

13. The absorbent structure according to claim 12, wherein the absorbent material layer has a density of 0.3–0.85 $g/cm^3$.

* * * * *